United States Patent
Whiteside et al.

(10) Patent No.: US 9,918,842 B1
(45) Date of Patent: Mar. 20, 2018

(54) KNEE SYSTEM

(75) Inventors: Leo A. Whiteside, Chesterfield, MO (US); Louis A. Serafin, Jr., Lakeport, MI (US)

(73) Assignee: Signal Medical Corporation, Marysville, MI (US)

( * ) Notice: Subject to any disclaimer, the term of this patent is extended or adjusted under 35 U.S.C. 154(b) by 1560 days.

(21) Appl. No.: 12/928,453

(22) Filed: Dec. 10, 2010

Related U.S. Application Data

(60) Provisional application No. 61/284,302, filed on Dec. 16, 2009, provisional application No. 61/284,656, filed on Dec. 22, 2009.

(51) Int. Cl.
*A61F 2/38* (2006.01)

(52) U.S. Cl.
CPC ..................... *A61F 2/38* (2013.01)

(58) Field of Classification Search
CPC ........................................ A61F 2/38
USPC ............. 623/20.14, 20.15, 20.21–20.29, 623/20.32–20.36, 23.15, 23.18, 23.24, 623/23.44
See application file for complete search history.

(56) References Cited

U.S. PATENT DOCUMENTS

| | | | |
|---|---|---|---|
| 5,194,066 A * | 3/1993 | Van Zile | 623/20.15 |
| 5,453,227 A | 9/1995 | Rieger | |
| 5,755,805 A | 5/1998 | Whiteside | 623/22 |
| 7,981,160 B1 * | 7/2011 | Serafin et al. | 623/22.25 |
| 2002/0006532 A1 * | 1/2002 | Robin | 428/697 |
| 2004/0049285 A1 * | 3/2004 | Haas | 623/20.15 |
| 2006/0025866 A1 | 2/2006 | Serafin, Jr. et al. | |
| 2006/0030945 A1 * | 2/2006 | Wright | 623/20.15 |
| 2012/0010722 A1 | 1/2012 | Walter et al. | |
| 2015/0297208 A1 | 10/2015 | Ahn | |

OTHER PUBLICATIONS

Smith & Nephew eCatalog—Profix Total Knee System, Nonporous and Porous Femaval Components, Long Stem Trials, 4 pp. Prod. 1990s, pt. Dec. 18, 2009.
Whiteside Biomechanics—Product Catalog, Quatroloc® Femoral System, 6 pp., 2002, printed Dec. 16, 2009.
USPTO Patent Full-Text and Image Database, Patent Database Search Results, first page of hits (1-18), ACLM/optionally: 105503 patents, Apr. 1, 2014.
Simpler Implant Solutions, "Morse Taper Mating Surface," www.simplerimplants.com, 2014, 1 page, printed Dec. 19, 2014.
Homestead, "Making a Morse Taper Center or Arbor," tool20895.homestead.com/filed/MORSE1.htm, 1 page, printed Dec. 19, 2014.
North Carolina Woodworker, Inc., "Lathe spindle morse taper at headstock . . . How to clean superficial rust inside the taper?" www.ncwoodworker.net/forums, Jul. 16, 2014, pp. 1-2/15, printed Dec. 19, 2014.
McKechine et al. (Eds.), Webster's New Universal Unabridged Dictrionary, Deluxe Second Edition, Dorest & Baber, Cleveland, Ohio, 1983 A.D., pp. 1578 and 1715.

(Continued)

*Primary Examiner* — Yashita Sharma
(74) *Attorney, Agent, or Firm* — Christopher John Rudy

(57) ABSTRACT

Femoral and/or tibial knee implant component includes a body and an elongate stem. The stem, at least for a substantial portion, has a polygonal shape when taken in cross-section generally perpendicular to its length. Modularity can be provided.

13 Claims, 2 Drawing Sheets

(56) References Cited

OTHER PUBLICATIONS

Oberg et al., Horton (Ed.), Machinerys Handbook, Fifteenth Edition, The Industrial Press, New York, New York, 1956 A.D., pp. 1318 and 1411-1413.
Mish et al. (Eds.), Webster's Ninth New Collegiate Dictionary, Merriam-Webster Inc., Springfield, Mass., 1984, p. 1114.
Wikipedia, the free encyclopedia, "Machine taper," en.wikipedia.org, last modified Mar. 24, 2016, 12 pages.

* cited by examiner

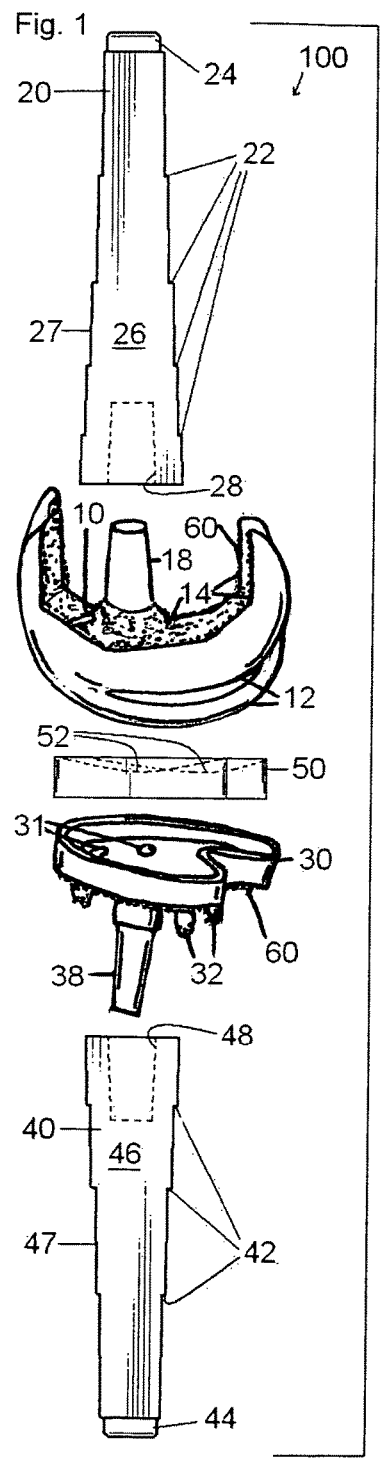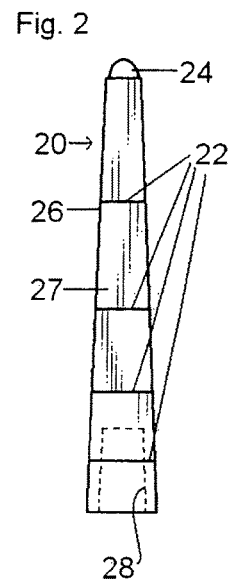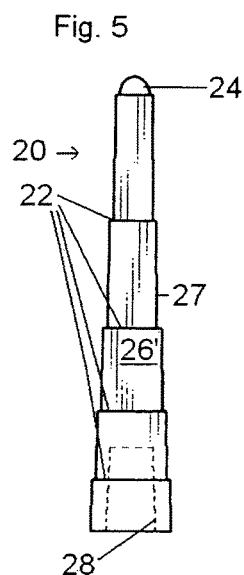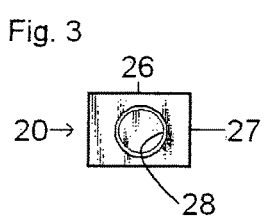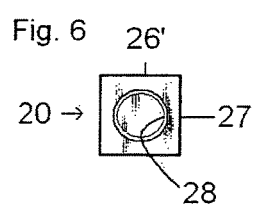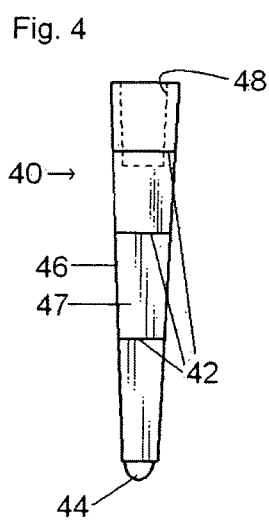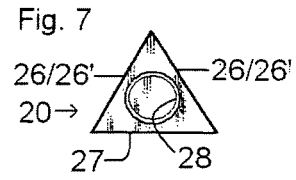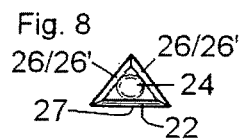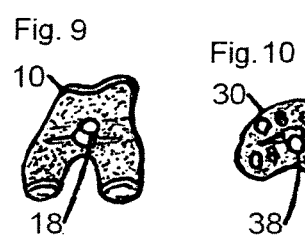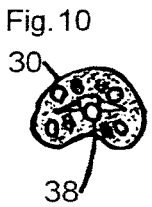

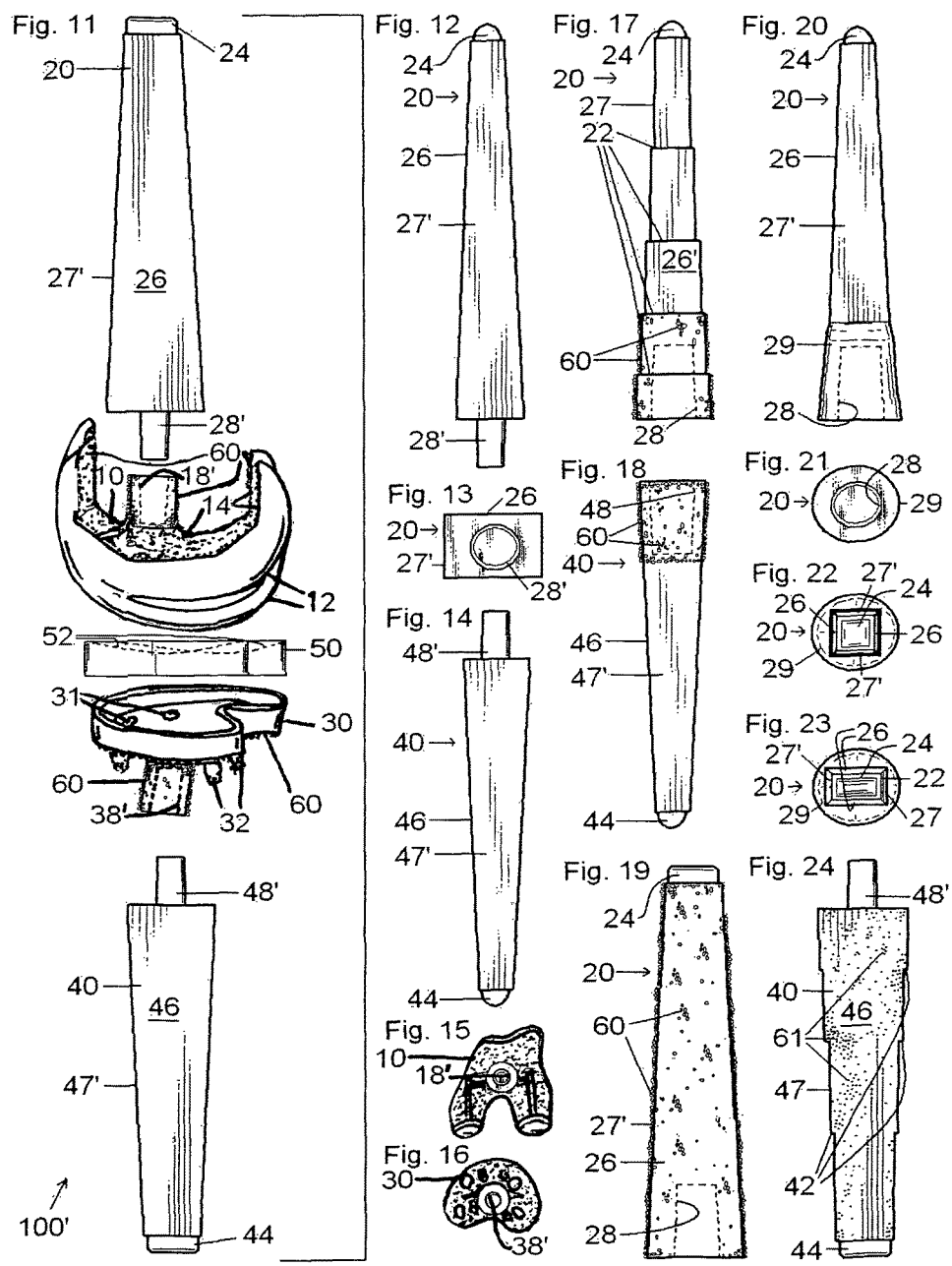

US 9,918,842 B1

KNEE SYSTEM

This claims benefits under 35 USC 119(e) of provisional application Nos. U.S. 61/284,302 filed on Dec. 16, 2009 A.D., and U.S. 61/284,656 filed on Dec. 22, 2009 A.D. The complete specifications of those applications are incorporated herein by reference.

FIELD AND PURVIEW OF THE INVENTION

This concerns a knee joint implant system, which has at least one of a femoral and a tibial component, in which at least one of the components has an elongate stem, which, at least for a substantial portion, has a polygonal shape when taken in cross-section generally perpendicular to the length of the stem. The system can be modular, particularly with respect to the stem.

BACKGROUND TO THE INVENTION

Various knee joint implant components are known, some of which can have femoral and/or tibial components equipped with stem(s) to insert into a corresponding intramedullary canal. In such knee systems, stem cross-sectional shapes perpendicular to the length of the stem are known to be generally circular or to have flutes.

On the other hand, the known Quatroloc® femoral total hip component has a generally tapering stem with a rectangular cross-section taken perpendicular generally to its length. It also has stepped shoulders (ridges with sharp distal or leading edges to form cutting steps) along its tapering length. Compare, Whiteside, U.S. Pat. No. 5,755,805.

The knee is a peculiarly created joint, unlike any other in the body. It articulates in numerous ways, and as a result, knee implant replacement joint components may be subject to instability, to include with respect to rotation of any stem in the intramedullary canal of the femur or tibia. As well, various configurations of knee implant replacement joint components may engender instability from inadequate or excessive stress on cortical bone structure, which may weaken, cause necrosis of, or even break the bone, and cause instability. But see, the noted '805 patent to Whiteside, e.g., column 6, lines 14-19, etc.

It would be desirable to ameliorate if not completely solve drawbacks in the art of knee joint replacement implants. It would be desirable to provide the art an alternative.

A FULL DISCLOSURE OF THE INVENTION

The present invention provides a knee system, which comprises a femoral and/or tibial component, which includes a body and an elongate stem, wherein the stem, which, at least for a substantial portion of the stem, has a polygonal shape when taken in cross-section generally perpendicular to the length of the stem. The system can be modular, particularly with respect to the stem.

The invention is useful in arthroplasty.

Significantly, by the invention, the art is improved in kind. One or more problems in the art of knee joint replacement implants is or are ameliorated if not completely solved, and an alternative is provided the art. The component is secured from rotation in the intramedullary canal by way of its polygonal cross-section. Moreover, more adequate stress can be placed on cortical bone structure along the length of the stem from its tapered elongate shape, plus with any shoulders along the way, thus preserving bone from absorptive loss and so strengthening the implant and increasing its stability in the bone in which the implant component is implanted.

Numerous further advantages attend the invention.

The drawings form part of the specification hereof. With respect to the drawings, which are not necessarily drawn to scale, the following is briefly noted:

FIG. 1 is an exploded side plan view of an instant knee system embodiment.

FIG. 2 is a front or rear plan view of the femoral stem in the implant of FIG. 1, taken perpendicularly to the view of FIG. 1.

FIG. 3 is a bottom view (looking from the distal to the proximal direction) of the femoral stem of FIG. 2. This can also serve as a top view (looking from the proximal to the distal direction) of a tibial stem such as the tibial stem in FIGS. 1 and 4. This depicts a rectangular cross-sectional shaped, tapering, shouldered stem.

FIG. 4 is a front or rear plan view of the tibial stem in the implant of FIG. 1, taken perpendicularly to the view of FIG. 1.

FIG. 5 is a front or rear plan view of another embodiment of an elongate stem, which can be employed in the implant of FIG. 1, for example, as a femoral stem, and which also has a side plan view as in FIG. 2. The view of the present figure is taken perpendicularly to the view of FIG. 2.

FIG. 6 is a bottom view (looking from the distal to the proximal direction) of the stem of FIG. 5. This depicts a square cross-sectional shaped tapering, shouldered stem, and can also serve as a top view (looking from the proximal to the distal direction) of a corresponding tibial stem.

FIG. 7 is a bottom view (looking from the distal to the proximal direction) of another embodiment of an elongate stem for a femoral (or tibial) component. This illustrates a triangular cross-sectional shaped, tapering, shouldered stem, and can also serve as a top view (looking from the proximal to the distal direction) of a corresponding tibial stem.

FIG. 8 is a top view of the stem of FIG. 7.

FIG. 9 is a top view (looking from the proximal to the distal direction) of the femoral component body shown within FIG. 1.

FIG. 10 is a bottom view (looking from the distal to the proximal direction) of the tibial component body shown within FIG. 1.

FIG. 11 is an exploded side plan view of another knee system embodiment.

FIG. 12 is a front or rear view of the femoral stem in the implant of FIG. 11, taken perpendicularly to the view of FIG. 11.

FIG. 13 is a bottom view (looking from the distal to the proximal direction) of the femoral stem of FIG. 12. This can also serve as a top view (looking from the proximal to the distal direction) of a tibial stem such as the tibial stem in FIGS. 11 and 14. This depicts a rectangular cross-sectional shaped, tapering, shouldered stem.

FIG. 14 is a front or rear view of the tibial stem in the implant of FIG. 11, taken perpendicularly to the view of FIG. 11.

FIG. 15 is a top view (looking from the proximal to the distal direction) of the femoral component body shown within FIG. 11.

FIG. 16 is a bottom view (looking from the distal to the proximal direction) of the tibial component body shown within FIG. 11.

FIG. 17 is a front or rear plan view of another embodiment of an elongate stem, which can be employed in the implant of FIG. 1, for example, as a femoral stem, and which also has a side plan view generally as in FIG. 2. Compare, FIGS. 5 and 6. This embodiment, however, has a porous coating over a portion of the stem.

FIG. 18 is a front or rear plan view of a tibial stem employable in the implant of FIG. 1. This depicts a square cross-sectional shaped, tapering, non-shouldered stem. This embodiment has a porous coating over a portion of the stem.

FIG. 19 is a side plan view of a femoral stem, which can be employed in the implant of FIG. 1. This depicts a rectangular cross-sectional shaped, tapering, non-shouldered stem, which has a porous coating over its sides.

FIG. 20 is a side plan view of a femoral stem, which can be employed in the implant of FIG. 1. This depicts a square cross-sectional shaped, tapering, non-shouldered portion to the stem having a round distal end blended into that generally square portion.

FIG. 21 is a bottom view (looking from the distal to the proximal direction) of the femoral stem of FIG. 20. This can also serve as a top view (looking from the proximal to the distal direction) of a corresponding tibial stem.

FIG. 22 is a top view of (looking from the proximal to the distal direction) of the femoral stem of FIG. 20. This can also serve as a bottom view (looking from the proximal to the distal direction) of a corresponding tibial stem.

FIG. 23 is a top view of (looking from the proximal to the distal direction) of the femoral stem such as of FIG. 20 but having a rectangular cross-sectional shaped, tapering, non-shouldered portion to the stem with a round distal end blended into that generally rectangular portion. This can also serve as a bottom view (looking from the proximal to the distal direction) of a corresponding tibial stem.

FIG. 24 is a front or rear plan view of a tibial stem employable in the implant of FIG. 11. This depicts a rectangular cross-sectional shaped, tapering, shouldered stem, which is grit blasted over at least the non-shouldered, outside sides of the stem, save those portions on the tip, on its bottom, and in its receptacle.

The invention can be further understood by the detail set forth below. As with the foregoing disclosure mentioned above, the following is to be taken in an illustrative and not necessarily limiting sense.

The present knee system embraces a femoral component and/or tibial component. When present, the component of interest includes a body and an elongate stem. The stem has at least a substantial portion with polygonal shape when taken in cross-section generally perpendicular to its length. The system can be modular, particularly with respect to the stem. The system can be not modular, particularly with respect to the stem; in such a case, the body and stem are not interchangeable with other bodies or stems.

With respect to the drawings, knee system 100, 100' can include a femoral component and/or a tibial component. Any suitable materials may be employed, and various components can have any configuration and size appropriate for the patient.

Femoral component frame 10, say, of a suitable metal such as a biocompatible cobalt-chrome alloy or suitable ceramic such as magnesium oxide transformation toughened zirconia (MgO-TTZ), serves as the femoral component body. It includes condyle surfaces 12 for articulation; back portion 14; and trunnion 18, which, say, may be provided with a suitable taper such as a Morse taper. In lieu of the trunnion 18, the frame 10 may have tapered receptacle 18'.

Femoral component stem 20, say, of a suitable metal such as a biocompatible cobalt-chrome or titanium-containing alloy (e.g., 6-1) or suitable ceramic such as MgO-TTZ, is elongate and tapered along its length. It includes stepped shoulders 22; tip 24, which can be rounded; first side 26, which is flat, and can have a corresponding opposing flat side, or first side 26', which is stepped to include shoulders 22, which may be sharp and capable of cutting into cortical bone, along its face, either of which can be opposed by a corresponding stepped side or a flat face; second side 27, which is stepped to include the shoulders 22, which, again, may be sharp and capable of cutting into cortical bone, or second side 27', which is flat, either of which can be opposed by a corresponding stepped side or flat face; and tapered receptacle 28, which receives the trunnion 18 and secures the femoral component frame 10 to the femoral component stem 20. In lieu of the tapered receptacle 28, the femoral component stem 20 may have trunnion 28', which, say, may be provided with a suitable taper such as a Morse taper, which can be inserted and secured in the tapered receptacle 18'. Rounded end 29, say, conically tapered to a slight degree, can be blended into the remainder of the substantially polygonal stem 20.

Tibial component tray 30, say, of a suitable metal such as a biocompatible titanium-containing alloy (e.g., 6-1) or suitable ceramic such as MgO-TTZ, serves as the tibial component body. It can include mounting screw holes 31; resected bone-face securing spikes 32; and trunnion 38, which, say, may be provided with a suitable taper such as a Morse taper. In lieu of the trunnion 38, the frame 30 may have tapered receptacle 38'.

Tibial component stem 40, say, of a suitable metal such as a biocompatible cobalt-chrome or titanium-containing alloy (e.g., 6-1) or suitable ceramic such as MgO-TTZ, is elongate and tapered along its length. It includes stepped shoulders 42; tip 44, which can be rounded; first side 46, which is flat, and can have a corresponding opposing flat side, or first side 46', which is stepped to include shoulders 42, which may be sharp and capable of cutting into cortical bone, along its face, either of which can be opposed by a corresponding stepped side or a flat face; second side 47, which is stepped to include the shoulders 42, which, again, may be sharp and capable of cutting into cortical bone, or second side 47', which is flat, either of which can be opposed by a corresponding stepped side or flat face; and tapered receptacle 48, which receives the trunnion 38 and secures the tibial component tray 30 to the tibial component stem 40. In lieu of the tapered receptacle 48, the tibial component stem 40 may have trunnion 48', which, say, may be provided with a suitable taper such as a Morse taper, which can be inserted and secured in the tapered receptacle 38'. A rounded end akin to the femoral component stem end 29 can be blended into the remainder of the substantially polygonal tibial component stem.

The engaging surfaces of the tapered trunnions 18, 28', 38, 48' and tapered receptacles 18', 28, 38', 48 can be smooth such as found with Morse tapers. Compare FIGS. 1-7, 9-21 and 24.

Tibial tray liner 50, say, of ultra high molecular weight polyethylene (UHMWPE), conforms to and is insertable for securement in the tibial tray. It includes articulation surfaces 52 upon each of which articulates a respective condyle 12 of the femoral component frame 10.

The knee system can be a knee joint implant system, wherein the femoral component includes one and only one body 10 and one and only one stem 20, and the tibial component includes one and only one body 30 and one and only one stem 40. See, FIGS. 1 and 11.

A surface or material for engendering bone ingrowth can be provided. Thus, porous coating 60 and/or grit-blasted surface 61, and/or a material such as hydroxyapatite may be provided for bone ingrowth.

The knee system can be for a human being.

Various sizes and configurations of bodies and stems may be provided for modular mix and match assembly to match the human patient. A suitably sized and configured femoral stem may be employed as a tibial stem and vice versa. Such bodies and stems may be provided in a kit, which may also include tools for assisting with surgical implantation of the implant.

The present invention is thus provided. Various feature(s), part(s), step(s), subcombination(s) and/or combination(s) may be employed with or without reference to other feature(s), part(s), step(s), subcombination(s) and/or combination(s) in the practice of the invention, and numerous adaptations and modifications can be effected within its spirit, the literal claim scope of which is particularly pointed out as follows:

What is claimed is:

1. A knee joint implant system, which comprises at least one of a femoral component and a tibial component, wherein the femoral component includes one and only one body and one and only one stem, and the tibial component includes one and only one body and one and only one stem, and wherein:
    the stem for the femoral component is of one and only one piece, with an exterior thereof for direct contact with bone in an intramedullary canal of a femur, is elongate and has a length, and, at least for a substantial portion, has a polygonal exterior shape when taken in cross-section generally perpendicular to the length of the stem for the femoral component;
    the stem for the tibial component is of one and only one piece, with an exterior thereof for direct contact with bone in an intramedullary canal of a tibia, is elongate and has a length, and, at least for a substantial portion, has a polygonal exterior shape when taken in cross-section generally perpendicular to the length of the stem for the tibial component; and
    the body and the stem for the femoral component, and the body and the stem for the tibial component are individual knee joint replacement implant component pieces that can be assembled to each other, to include with the body and the stem for the femoral component assembled to one another and the body and the stem for the tibial component assembled to one another, such that the system is modular; and
further wherein:
    the femoral component includes a femoral component frame of one and only one piece that serves as the body for the femoral component, which includes condyle surfaces for articulation, a back portion, and a tapered femoral component receptacle having a smooth first engaging surface in the femoral component frame for receiving a corresponding tapered femoral component trunnion having a smooth second engaging surface of the stem for the femoral component;
    the stem for the femoral component extends along a lengthwise axis, is tapered along its length, and includes stepped shoulders, a tip, and a first flat side that includes at least a portion of the stepped shoulders; and the tapered femoral component trunnion having the smooth second engaging surface, which can be inserted in the tapered femoral component receptacle having the smooth first engaging surface of the body for the femoral component and secured thereby;
    the tibial component includes a tibial component tray of one and only one piece that serves as the body for the tibial component, and a tapered tibial component receptacle having a smooth third engaging surface in the tibial component tray for receiving a corresponding tapered tibial component trunnion having a smooth fourth engaging surface of the stem for the tibial component; and
    the stem for the tibial component extends along a lengthwise axis, is tapered along its length, and includes stepped shoulders, a tip, and a first flat side that includes at least a portion of the stepped shoulders; and the tapered tibial component trunnion having the smooth fourth engaging surface, which can be inserted in the tapered tibial component receptacle having the smooth third engaging surface of the body for the tibial component and secured thereby.

2. The system of claim 1, wherein the body and the stem of said at least one component are made from magnesium oxide transformation toughened zirconia.

3. The system of claim 1, wherein at least one of the following features is provided:
    both the femoral and tibial components are present; and
    the tibial component tray is provided with a liner, which conforms to and is insertable for securement in the tibial component tray opposite the stem for the tibial component and includes articulation surfaces upon which articulates a respective condyle of the femoral component frame.

4. The system of claim 1, wherein the polygonal shape is a quadrilateral or a triangle.

5. The system of claim 1, wherein the polygonal shape is a rectangle.

6. The system of claim 5, wherein there are two opposing stepped faces and two opposing generally flat faces.

7. The system of claim 1, wherein a surface for engendering bone ingrowth is provided.

8. The system of claim 1, wherein each trunnion and receptacle is provided with a Morse taper.

9. A knee joint implant system, which comprises at least one of a femoral component and a tibial component, wherein the femoral component includes one and only one body and one and only one stem, and the tibial component includes one and only one body and one and only one stem, with the body and the stem for the femoral component, and the body and the stem for the tibial component being individual knee joint replacement implant component pieces that can be assembled to one another such that the system is modular, wherein:
    the femoral component includes a femoral component frame of one and only one piece that serves as the body for the femoral component, which includes condyle surfaces for articulation, a back portion, and, as part of the femoral component frame, a tapered femoral component receptacle having a smooth first engaging surface for receiving a corresponding tapered femoral component trunnion having a smooth second engaging surface of the stem for the femoral component;
    the stem for the femoral component is of one and only one piece; with an exterior thereof for direct contact with bone in an intramedullary canal of a femur; is elongate; has a length; has, at least for a substantial portion, a rectangular, external shape when taken in cross-section generally perpendicular to its length; extends along a lengthwise axis and is tapered along its length; and includes two opposing faces having stepped shoulders and two opposing faces that are generally flat and provided with a surface for engendering bone ingrowth; a tip; and the tapered femoral component trunnion having the smooth second engaging surface, which can be inserted in the tapered femoral component receptacle having the smooth first engaging surface of the body for the femoral component and secured thereby;

the tibial component includes a tibial component tray of one and only one piece that serves as the body for the tibial component, and, as part of the tibial component tray, a tapered tibial component receptacle having a smooth third engaging surface for receiving a corresponding tapered tibial component trunnion having a smooth fourth engaging surface of the stem for the tibial component;

the stem for the tibial component is of one and only one piece; with an exterior thereof for direct contact with bone in an intramedullary canal of a tibia; is elongate, has a length; has, at least for a substantial portion, a rectangular, external shape when taken in cross-section generally perpendicular to its length; extends along a lengthwise axis and is tapered along its length; and includes two opposing faces having stepped shoulders and two opposing faces that are generally flat and provided with a surface for engendering bone ingrowth; a tip; and the tapered tibial component trunnion having the smooth fourth engaging surface, which can be inserted in the tapered tibial component receptacle having the smooth third engaging surface of the body for the tibial component and secured thereby; and each trunnion and receptacle has a length significantly less than one half the length of the respective stem.

10. The system of claim 9, wherein the body and the stem of said at least one component are made from magnesium oxide transformation toughened zirconia.

11. The system of claim 9, wherein the surface for engendering bone ingrowth includes a grit blasted surface.

12. The system of claim 9, wherein the surface for engendering bone ingrowth includes a porous coating.

13. The system of claim 9, wherein each trunnion and receptacle is provided with a Morse taper.

\* \* \* \* \*